United States Patent
Watanabe

(10) Patent No.: US 12,220,248 B2
(45) Date of Patent: Feb. 11, 2025

(54) INFORMATION PROCESSING APPARATUS AND INFORMATION PROCESSING METHOD

(71) Applicant: Panasonic Intellectual Property Management Co., Ltd., Osaka (JP)

(72) Inventor: Kazuhiro Watanabe, Tokyo (JP)

(73) Assignee: PANASONIC INTELLECTUAL PROPERTY MANAGEMENT CO., LTD., Osaka (JP)

( * ) Notice: Subject to any disclaimer, the term of this patent is extended or adjusted under 35 U.S.C. 154(b) by 0 days.

(21) Appl. No.: 17/770,689

(22) PCT Filed: Jun. 10, 2021

(86) PCT No.: PCT/JP2021/022035
§ 371 (c)(1),
(2) Date: Apr. 21, 2022

(87) PCT Pub. No.: WO2022/059273
PCT Pub. Date: Mar. 24, 2022

(65) Prior Publication Data
US 2022/0378367 A1 Dec. 1, 2022

(30) Foreign Application Priority Data
Sep. 17, 2020 (JP) .................. 2020-156547

(51) Int. Cl.
*A61B 5/107* (2006.01)
*A61B 5/00* (2006.01)
(52) U.S. Cl.
CPC ............ *A61B 5/4809* (2013.01); *A61B 5/107* (2013.01)
(58) Field of Classification Search
CPC ... A61B 5/4809; A61B 5/107; A61B 5/14552; A61B 5/145; A61B 5/1455;
(Continued)

(56) References Cited

U.S. PATENT DOCUMENTS 11,134,888 B2 * 10/2021 Wright .................. G05B 15/02
2014/0280051 A1 9/2014 Djugash
(Continued)

FOREIGN PATENT DOCUMENTS

| CN | 112000021 A | * 11/2020 |
|----|----|----|
| HK | 1218045 A | * 6/2016 |
| JP | 2007-241503 A | 9/2007 |
| JP | 2014-135616 A | 7/2014 |
| JP | 2014-179103 A | 9/2014 |
| JP | 2015-170110 A | 9/2015 |
| JP | 2015-195023 A | 11/2015 |

(Continued)

OTHER PUBLICATIONS

International Search Report issued in corresponding International Application No. PCT/JP2021/022035, dated Sep. 7, 2021 w/English Translation.

*Primary Examiner* — James J Yang
*Assistant Examiner* — Anthony D Afrifa-Kyei
(74) *Attorney, Agent, or Firm* — Rimon P.C.

(57) ABSTRACT

A management apparatus includes an obtainer that obtains detected information from a sensor that detects sleep of a user; a sleep determiner that determines whether the user is in a sleep state, based on the detected information; a manager that is connected to an appliance via a network, and obtains state information indicating an operation state of the appliance; an appliance determiner that determines whether the state information is different from predetermined normal information indicating a normal operation state of the appliance, when the sleep determiner determines that the user is in the sleep state; and a notification controller that outputs a notification signal, when the appliance determiner determines that the state information is different from the normal information.

12 Claims, 10 Drawing Sheets

(58) Field of Classification Search
CPC ... A61B 5/14551; A61B 5/103; A61B 5/4806;
A61B 5/681; A61B 5/6826; A61B
5/6838; A61B 2562/222; A61B 5/6825;
H04L 41/085; H04L 12/2803; H04L
41/0622; H04L 41/0636; H04L 41/064;
H04L 41/065; H04L 41/0866; G05B
23/0254; G05B 23/00; G05B 23/02;
G05B 23/0205; G05B 23/0218; G05B
23/0243; G05B 2219/1196; G05B
2219/25428; G05B 2219/31211; G05B
2219/34012; G06F 11/22; G06F 18/24;
G06F 18/295; G06K 9/6267; G08C
17/02; H02J 50/80; H04Q 9/00; H04Q
9/02; H04Q 9/04; H04Q 9/06; H04Q
9/08; H04Q 9/14

See application file for complete search history.

(56) References Cited

U.S. PATENT DOCUMENTS

| | | | |
|---|---|---|---|
| 2015/0281891 | A1 | 10/2015 | Umetani et al. |
| 2016/0261425 | A1* | 9/2016 | Horton ............... H04L 12/2803 |
| 2017/0235542 | A1* | 8/2017 | Watanabe ............ G06F 3/165 |
| | | | 700/94 |
| 2018/0315294 | A1 | 11/2018 | Takano |

FOREIGN PATENT DOCUMENTS

| | | | | |
|---|---|---|---|---|
| JP | 2017-127373 | A | | 7/2017 |
| JP | 2017-143478 | A | | 8/2017 |
| JP | 6577642 | B2 | | 8/2019 |
| KR | 20120051122 | A | * | 11/2010 |

* cited by examiner

FIG. 4

| Appliance | Operation state |
|---|---|
| Rice cooker | Keep warm |
| Dishwashing machine | Stop |
| Washing machine | Stop (with laundry) |
| ... | ... |

FIG. 5

| Appliance | Operation state |
|---|---|
| Rice cooker | Rice-cooking timer ON |
| Dishwashing machine | Washing |
| Washing machine | Stop |
| ... | ... |

FIG. 7

| Appliance | Operation state | Normal start-time | Normal end-time |
|---|---|---|---|
| Rice cooker | Rice-cooking timer ON | 23:00 | 6:00 |
| Dishwashing machine | Washing | 22:00 | 3:00 |
| Washing machine | Stop | 18:00 | — |
| ... | ... | ... | ... |

INFORMATION PROCESSING APPARATUS AND INFORMATION PROCESSING METHOD

CROSS REFERENCE TO RELATED APPLICATIONS

This application is the U.S. National Phase under 35 U.S.C. § 371 of International Application No. PCT/JP2021/022035, filed on Jun. 10, 2021, which claims the benefit of Japanese Application No. 2020-156547, filed on Sep. 17, 2020, the entire contents of each of which Applications are hereby incorporated by reference in their entirety.

TECHNICAL FIELD

The present disclosure relates to an information processing apparatus and an information processing method.

BACKGROUND ART

Conventionally, household electrical appliances including a washing machine, a rice cooker, and so on have been used. The household electrical appliances are each controlled to operate at an appropriate timing in accordance with an action of a user in his/her life.

There have conventionally been techniques of changing notifying ways depending on a sleep state of a user (see Patent literature (PTL) 1).

CITATION LIST

Patent Literature

[PTL 1] Japanese Unexamined Patent Application Publication No. 2017-127373

SUMMARY OF INVENTION

Technical Problem

If a user falls asleep without operating a household electrical appliance, the appliance does not operate in accordance with the user's intention.

In view of the above, the present disclosure provides an information processing apparatus that appropriately awakes a user for the operation of an appliance.

Solution to Problem

An information processing apparatus according to the present disclosure includes an obtainer that obtains detected information from a sensor that detects sleep of a user; a first determiner that determines whether the user is in a sleep state, based on the detected information; a manager that is connected to an appliance via a network, and obtains state information indicating an operation state of the appliance; a second determiner that determines whether the state information is different from predetermined normal information indicating a normal operation state of the appliance, when the first determiner determines that the user is in the sleep state; and a notification controller that outputs a notification signal, when the second determiner determines that the state information is different from the normal information.

According to the above aspect, the information processing apparatus detects that the user sleeps, and outputs the notification signal when the state of the appliance is different from the normal state. The situation in which the user sleeps and the state of the appliance is different from the normal state occurs when the user falls asleep without setting the appliance. In this case, if the user continuously sleeps without awaking and operating the appliance, the appliance may not operate in accordance with the user's intention at the time when the user awakes. In view of the situation, the information processing apparatus can awake the user and encourage the user to operate the appliance by performing the notification to the user. Accordingly, the information processing apparatus can appropriately awake the user for the operation of an appliance.

The first determiner may further determine whether the sleep state of the user is a first sleep state, based on the detected information obtained by the obtainer. The notification controller may output the notification signal, when the first determiner determines that the sleep state of the user is the first sleep state.

According to the above aspect, the information processing apparatus stimulates the user to awake by the notification, during the first sleep state in which a sleep depth is relatively light in the user's sleep. If a user is awoken from a sleep state in which the sleep depth is deep, it is typically difficult for the user to awake. Even if the user awakes, the quality of user's sleep deteriorates. Furthermore, if the user in the relatively deep sleep state is awoken, it may be difficult for the user to fall asleep again in spite of the intention of the user to have the sleep. This prevents the user from having the continuing sleep for a proper period of time. In addition, if a user in the relatively deep sleep state is awoken by the notification, a level of user's awareness (or consciousness level) is low. This may often cause a mistake in operations performed after the user awakes. In view of the above, a user is stimulated to be awoken during the first sleep state in which the sleep depth is relatively light, thereby being appropriately encouraged to operate an appliance after the user awakes. Accordingly, the information processing apparatus can more appropriately awake a user for the operation of the appliance.

The notification controller may output the notification signal, when the first determiner determines that the sleep state of the user is the first sleep state, in a transition of a sleep state of the user from an awareness state, through the first sleep state, to a second sleep state, the second sleep state being a state of deeper sleep than the first sleep state.

According to the above aspect, the information processing apparatus stimulates the awareness of a user by the notification, when the user is in the first sleep state. Accordingly, a user can be stimulated to be awoken and to operate appliances as early a time as possible. Accordingly, a user can have, after the operation, a sleep for a continuous period of time in the second sleep onset. As mentioned above, the information processing apparatus can more appropriately awake a user for the operation of an appliances.

The first sleep state may include a non-rapid eye movement (NREM) sleep state at stage 1 and stage 2. The second sleep state may include a NREM sleep state at stage 3 and stage 4.

According to the above aspect, the information processing apparatus can appropriately awake a user for the operation of an appliance, in view of a sleep state of the user among the respective stages in rapid eye movement (REM) sleep and the NREM sleep.

The normal information may include a normal period in which the appliance should be operating in the normal operation state. The first determiner may further: obtain a sleep start time at which a state of the user transitions from an awareness state to the first sleep state, based on the detected information obtained by the obtainer; and makes a first determination as to whether the state information at the sleep start time obtained is different from the normal information, and a second determination as to whether a sleep end presumption time at which a normal sleep period has elapsed from the sleep start time obtained is later than the normal period. The notification controller may output the notification signal, when the first determiner determines, regarding the first determination, that the state information is different from the normal information, and determines, regarding the second determination, that the sleep end presumption time is later than the normal period.

According to the above aspect, in the information processing apparatus, if a user falls asleep when the operation state of the appliance is different from the normal state, the information processing apparatus essentially awakes the user. However, if no problem occurs with the user operating appliances after he/she awakes, the information processing apparatus performs control so as not to awake the user exceptionally. This is because, if no problem occurs with the user operating appliances after he/she awakes, there is no need to awake the user at the time when the user starts sleeping for the operation of an appliance. Accordingly, the information processing apparatus can more appropriately awake a user for the operation of the appliance.

The second determiner may further determine a room where the user is present, based on the state information obtained by the manager. The notification controller may output the notification signal for notifying the user, via a speaker provided in the room where the user is present.

According to the above aspect, the information processing apparatus performs the notification to a user, using the speaker device in the room where the user is present. Accordingly, the user can more appropriately be awoken. In addition, the notification is not performed using a speaker device in a room different from the room where the user is present, thereby contributing to the reduction in throughput and power consumption. Accordingly, the information processing apparatus can more appropriately awake a user for the operation of an appliance.

The notification controller may prohibit outputting the notification signal when the user is determined to be present in a bedroom.

According to the above aspect, the information processing apparatus refrains from performing the notification when a user is sleeping in the bedroom. In the case where a user is sleeping in the bedroom, the user may have a reason for prioritizing the sleep. It may be improper to awake the user even in such a situation. Accordingly, the information processing apparatus can awake a user for the operation of an appliance depending on the condition of the user.

The information may further include an appliance controller that causes the appliance in a room where the user is present to set an environment in the room to be suitable for the sleep of the user, when the first determiner determines that the user is in the sleep state and the second determiner determines that the state information obtained by the manager matches the normal information.

According to the above aspect, when the state of an appliance is identical to the normal state, the information processing apparatus leaves the user to continue sleeping, and sets up an environment in which the user comfortably sleeps by controlling the appliance. Accordingly, the information processing apparatus can appropriately awake a user for the operation of an appliance, whereas it can appropriately leave the user to sleep when there is no need to operate an appliance.

The sensor may include at least a heartbeat sensor, an acceleration sensor, a thermal image sensor, or a radio wave sensor.

According to the above aspect, the information processing apparatus can appropriately awake a user for the operation of an appliance, in an easier manner using the heartbeat sensor, the acceleration sensor, the thermal image sensor, or the radio wave sensor.

An information processing method according to the present disclosure includes: obtaining detected information from a sensor that detects sleep of a user; first determining whether the user is in a sleep state based on the detected information; obtaining state information indicating an operation state of an appliance connected to a network; second determining whether the state information is different from predetermined normal information indicating a normal operation state of the appliance, when it is determined that the user is in the sleep state in the first determining; and outputting a notification signal, when it is determined that the state information is different from the normal information in the second determining.

According to the above aspect, the effects same as those obtained by the information processing apparatus are obtained.

It should be noted that these comprehensive or specific aspects may be embodied by a system, a method, an integrated circuit, a computer program, a computer-readable recording medium such as a CD-ROM, or any combination of the system, the method, the integrated circuit, the computer program, and the recording medium.

Advantageous Effects of Invention

An information processing apparatus according to the present disclosure can appropriately awake a user for operation of an appliance.

BRIEF DESCRIPTION OF DRAWINGS

FIG. 4 is an explanatory view showing an example of state information according to Embodiment 1.

FIG. 5 is an explanatory view showing an example of normal information according to Embodiment 1.

FIG. 7 is an explanatory view showing an example of normal information according to Embodiment 2.

DESCRIPTION OF EMBODIMENTS

Figure 1:
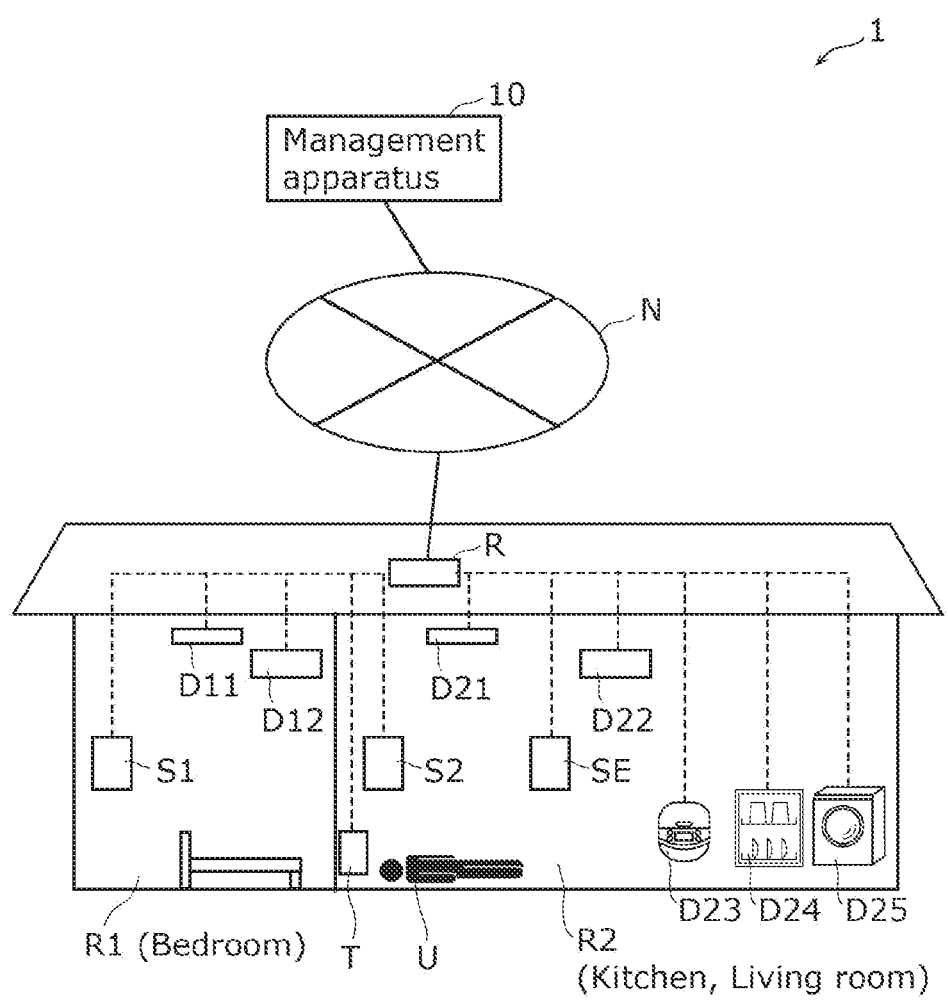
FIG. 1 is an explanatory view schematically showing a configuration of a system according to Embodiment 1.

Hereinafter, embodiments are described in detail, with appropriately referring to the drawings. Here, description that is precise beyond the necessity may be omitted. For example, detailed description for well known matters and duplicate description for substantially the same configuration may be omitted. This prevents the below description from being unnecessarily redundant, to facilitate the understanding of a person skilled in the art.

It should be noted that an inventor provides the accompanied drawings and the description below for a person skilled in the art to understand the present disclosure sufficiently, and thus does not intend to limit the subject matters recited in the scope of claims, by the present disclosure.

Hereinafter, a background of the present disclosure and a problem to be solved by the present disclosure are described in detail, and then embodiments are described.

Conventionally, household electrical appliances including a washing machine, a rice cooker, and so on have been used. The household electrical appliances are controlled to operate at an appropriate timing in accordance with an action of a user in his/her life.

If a user hangs out laundry in the morning, for example, it is necessary, in the previous night, to put detergent and the laundry before being washed into a washing machine, and to turn ON a timer for causing the washing machine to operate. If a user eats cooked white rice for breakfast, for example, it is necessary, in the previous night, to put white rice before being cooked into a rice cooker and to turn ON a timer of the rice cooker.

If household electrical appliances are used in the above-mentioned way and a user falls asleep without operating the appliances, the household electrical appliances do not operate in accordance with the user's intention.

In order to avoid such a situation, it is assumed the user is awoken by performing notification, in a case when the user falls asleep without operating appliances.

By the way, it may be appropriate for human beings to have continuing sleep for a proper period of time at a level of 7 hours, for example. Even if short-period sleep is taken multiple times and a total of such short-period sleep is longer than the proper sleep period, such short-period sleep in multiple times may not be proper for human beings. In addition, it is known that human beings have relatively light sleep in the early stage of proper-period sleep, and then have relatively deep sleep. Thereafter, the relatively light sleep and the relatively deep sleep are alternately repeated in a cycle at a level of one and a half hour.

Accordingly, if a user falls asleep without operating an appliance, it is desirable to wake the user at a relatively early stage of the sleep after the user starts sleeping (e.g., at a time point after few minutes to dozen minutes elapse), while the user is in a relatively light sleep state.

If a user who is in a relatively deep sleep state is awoken by the notification at a time point after several tens of minutes elapse from start of the sleep, it is difficult for the user to awake. Even if the user awakes, the quality of user's sleep thereafter deteriorates. Furthermore, if the user in the relatively deep sleep state is awoken, it may be difficult for the user to fall asleep again in spite of the intention of the user to have the sleep. This prevents the user from having the continuing sleep for a proper period of time. In addition, if a user in the relatively deep sleep state is awoken by the notification, a level of the user's awareness (or consciousness level) is low. This may often cause a mistake in operations performed after the user awakes.

As mentioned above, if a user falls asleep without operating appliances, household electrical appliances do not operate in accordance with the user's intention.

In view of the above, the present disclosure provides an information processing apparatus that appropriately awakes a user for operation of the appliances.

Embodiment 1

In the present embodiment, an information processing apparatus that awakes user U appropriately for operating appliances is described.

FIG. 1 is an explanatory view schematically showing a configuration of system 1 according to the present embodiment.

System 1 shown in FIG. 1 is a system that controls appliance D11 and so on in a residence of user U and awakes user U appropriately for operating appliances. The residence of user U includes room R1 (a bedroom) and room R2 (a kitchen and a living room).

As shown in FIG. 1, system 1 includes: management apparatus 10; appliances D11, D12, D21, D22, D23, D24, and D25 (they are also referred to as appliance D11 and so on); speakers S1 and S1 (they are also referred to as speaker S1 and so on); and sensor SE. User U has terminal T that may be included in system 1.

Appliance D11 and so on, speaker S1 and so on, sensor SE, and terminal T are connected to management apparatus 10 in a communicable manner via network N and router R.

Network N includes a mobile phone carrier network, a telephone line network using a telephone line or optical fibers, a local area network (LAN) (including wired LAN or wireless LAN), and so on. Network N may also include a network in which a plurality of the above networks are connected one another.

Router R is a network device provided in a residence of user U. Router R is connected to appliance D11 and so on, speaker S1 and so on, and sensor SE, in a communicable manner, as well as is connected to network N to relay the communication of management apparatus 10 with appliance D11 and so on, speaker S1 and so on, and sensor SE. The communication of appliance D11 and so on, speaker S1 and so on, and sensor SE with router R may be a wired communication (Ethernet, and so on) and a wireless communication (Wi-Fi standard, Bluetooth standard, NEC standard, and so on). If the wireless communication is used, router R further functions as a base station (an access point). Hereinafter, a case where the wireless communication is the Wi-Fi communication is described as an example.

Management apparatus 10 is an information processing apparatus that manages and controls operations of appliance D11 and so on. Management apparatus 10 appropriately awakes user U for operating appliance D11 and so on. Management apparatus 10 is a computer provided with a central processing unit (CPU), a memory, a communication interface, and so on. The CPU uses the memory to execute a predetermined program, thereby exhibiting the above functions. Detailed functions of management apparatus 10 are described later.

Appliance D11 and so on are provided in the residence of user U and are used by user U. Each of appliance D11 and so on is provided with a communication interface (i.e., a communication interface of Wi-Fi standard), and is connected to management apparatus 10 in a communicable manner via router R and network N. Appliance D11 and so on are controlled to perform the respective operations, by management apparatus 10 via communication therewith.

For example, appliance D11 is a lighting device provided in room R1, and appliance D12 is an air conditioner provided in room R1. For example, appliance D21 is a lighting device provided in room R2, appliance D22 is an air conditioner provided in room R2, appliance D23 is a rice cooker provided in room R2, appliance D24 is a dishwashing machine (tableware washing machine) provided in room R2, and appliance D25 is a washing machine provided in room R2.

Speaker S1 is a speaker device that outputs sound based on information received from the exterior of speaker S1. Speaker S1 includes at least a CPU, a memory, a speaker body, a communication interface, and so on, and operates in accordance with information processing which the CPU performs using the memory.

Speaker S1 is provided in room R1. Speaker S1 performs notifying to user U under control of management apparatus 10. Specifically, when speaker S1 receives a notification signal from management apparatus 10, speaker S1 outputs sound according to the notification signal. It is assumed that the outputted sound is heard by user U present in room R1. Speaker S1 is, for example, a network speaker or a smart speaker. If appliance D11 and so on provided in room R1 each include a speaker, the speaker provided in the appliance can be also used as speaker S1.

Speaker S2 is a speaker device having functions similar to those of speaker S1, and is provided in room R2. Speaker S2 performs, independently of speaker S1, notifying to user U under control of management apparatus 10.

Sensor SE detects sleep of user U. Sensor SE provides information that is detected (it may be also referred to as detected information) to management apparatus 10.

Sensor SE is, for example, a thermal image sensor that obtains a thermal image in a space where sensor SE is provided. This case is used as an example for the description. Sensor SE may be a heartbeat sensor, an acceleration sensor, a radio wave sensor, and so on, in addition to the thermal image sensor.

Sensor SE also serving as the thermal image sensor obtains a thermal image in a space, and provides the obtained thermal image to management apparatus 10 as the detected information. If user U is present in the aforementioned space, the thermal image contains information indicating a posture of user U seen from the position of sensor SE, based on a fact that a body temperature of user U is higher than temperatures of a wall, a floor, furniture, and so on around user U. Sensor SE serving as the thermal image sensor can also be used as a thermal image sensor included in an air conditioner, for example.

If sensor SE is a heartbeat sensor, sensor SE provides information relating to the obtained heartbeat of user U, such as a heart rate, to management apparatus 10. Sensor SE serving as the heartbeat sensor may be a wearable sensor that can be attached to the body of user U.

If sensor SE is an acceleration sensor, sensor SE provides the acceleration of a body part (e.g., an arm) of user U, to which sensor SE is attached, to management apparatus 10 as the detected information. Sensor SE serving as the acceleration sensor may be a wearable sensor that can be attached to the body of user U.

If sensor SE is a radio wave sensor, sensor SE sends a radio wave (e.g., a millimeter wave) to a peripheral space, and receives a reflected wave of the sent millimeter wave from the body of user U. Sensor SE measures a distance from the position of sensor SE to user U, based on the intention of the received reflection wave. Then, senser SE provides, to management apparatus 10, information indicating the position of user U, which is calculated based on the measured distance or based on the distance and a direction from which the radio wave comes. The radio wave which the radio wave sensor sends and receives may be a radio wave in Wi-Fi communication. In this case, sensor SE can receive the radio wave using antenna included in router R having functions of a base station.

Sensor SE may include a part or all of the various sensors described above.

Terminal T is a terminal device which user U has. Terminal T may be a computer terminal, a smartphone, a tablet terminal, and so on. The various sensors provided in terminal T may also be used as sensor SE. Terminal T may also be used as the speaker device.

Figure 2:
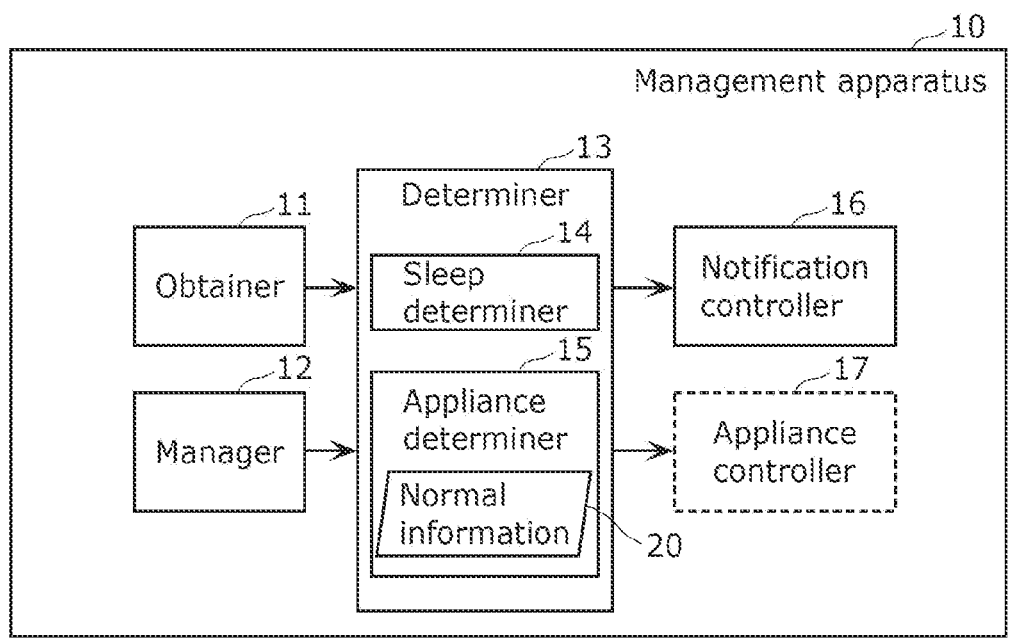
FIG. 2 is a block diagram showing a functional configuration of a management apparatus according to Embodiment 1.

FIG. 2 is a block diagram showing a functional configuration of management apparatus 10 according to the present embodiment.

As shown in FIG. 2, management apparatus 10 includes obtainer 11, manager 12, determiner 13, notification controller 16, and appliance controller 17. Appliance controller 17 is not an indispensable structural component. Management apparatus 10 has functional units each of which can be embodied in a manner that CPU provided in management apparatus 10 executes a predetermined program using a memory.

Obtainer 11 is a functional unit for obtaining detected information from sensor SE. Obtainer 11 provides, to determiner 13, the detected information that has been obtained. If sensor SE is a thermal image sensor, obtainer 11 obtains a thermal image as the detected information.

Manager 12 is a functional unit that obtains state information indicating an operation state of appliance D11 and so on. Appliance D11 and so on are used by user U, and are connected to management apparatus 10 (i.e., manager 12) via a network. Appliance D11 and so on from which manager 12 obtains the state information include at least an appliance indicated by normal information (described later). Manager 12 may receive a signal relating to the operation state from appliance D11 and so on at regular intervals to obtain the state information of appliance D11 and so on. Manager 12 may always receive a signal relating to the operation state from appliance D11 and so on to obtain the state information of appliance D11 and so on. Manager 12 may cause appliance D11 to send a signal relating to the operation state of appliance D11 to manager 12, to obtain the state information of appliance D11 and so on.

Manager 12 may receive a signal relating to the operation state of appliance D11, and presumes the state information of appliance D11 and so on, when the operation state of appliance D11 changes at a timing of the operation of appliance D11 and so on by user U or the action of appliance D11. Manager 12 may receive a signal relating to the operation state of appliance D11 at a certain interval, and may presume the state information of appliance D11 and so on.

Determiner 13 is a functional unit that performs determination processing. Determiner 13 includes sleep determiner 14 and appliance determiner 15.

Sleep determiner 14 is a functional unit that performs determination as to whether user U is sleeping, i.e., user U is in a sleep state. Sleep determiner 14 obtains the detected information which obtainer 11 obtains from sensor SE, and performs determination as to whether user U is sleeping based on the detected information obtained. For the determination, determination processing according to a type of the detected information is used. The detected information may be a thermal image obtained from sensor SE serving as the thermal image sensor. In such a situation, if sleep determiner 14 detects that user U lies in a room and does not move for a predetermined period of time (e.g., several minutes or about ten minutes), i.e., user U continuously takes a fixed posture, based on the information indicating the posture of user U seen from the position of sensor SE, sleep determiner 14 determines that user U sleeps. Sleep determiner 14 corresponds to a first determiner.

If the detected information relates to heartbeats obtained from sensor SE that is the heartbeat sensor and predetermined change is detected in information relating to the heartbeats, sleep determiner 14 determines that user U is sleeping. For example, when sleep determiner 14 detects decrease in a heart rate that is an example of the information relating to the heartbeat, sleep determiner 14 determines that user U sleeps.

If the detected information relates to the acceleration rate obtained from sensor SE that is the acceleration sensor and predetermined change is detected in the information relating to the acceleration, sleep determiner 14 determines that user U is sleeping. For example, when determiner 14 determines that the acceleration rate is smaller than a predetermined value, sleep determiner 14 determines that user U is sleeping.

If the detected information relates to a distance or a position obtained from sensor SE that is the radio wave sensor and a predetermined change is detected in the information relating to the distance or the position, sleep determiner 14 determines that user U is sleeping. For example, when sleep determiner 14 determines that the change in the distance or the position per a unit time is smaller than a predetermined value, sleep determiner 14 determines that user U is sleeping.

Appliance determiner 15 is a functional unit that performs determination processing regarding the operation state of appliance D11 and so on. When sleep determiner 14 determines that user U is in the sleep state, appliance determiner 15 determines whether the state information obtained by manager 12 is different from normal information 20. Here, normal information 20 is predetermined information indicating a normal operation state of appliance D11 and so on. For example, normal information 20 is predetermined information indicating the normal operation state of appliance D11 and so on at the time when user U goes to bed. This case is used as an example for the disclosure. Appliance determiner 15 corresponds to a second determiner.

If operation states of a plurality of appliances are indicated in normal information 20 in the above determination, appliance determiner 15 performs the determination on each of the plurality of the appliances.

Notification controller 16 is a functional unit that outputs a notification signal for notifying user U. When appliance determiner 15 determines that the state information is different from normal information 20, notification controller 16 outputs the notification signal for notifying user U. The notification signal is outputted to, for example, speaker S1 and so on, and includes a sound signal relating to sound that speaker S1 and so on output to user U. It is assumed that speaker S1 and so on that have received the notification signal outputs sound corresponding to the sound signal contained in the received notification signal.

Normal information 20 may indicate the operation states of a plurality of appliances, and the aforementioned determinations may be performed on each of the plurality of the appliances by appliance determiner 15. In such a case, notification controller 16 outputs the notification signal when it is determined that the state information relating to at least one appliance among the plurality of the appliances is different from normal information 20. In this case, the sound signal indicating the above-described at least one appliance may be contained in the notification signal. For example, if the state information of the rice cooker is different from "rice-cooking timer ON" that is normal information 20, the notification signal may contain the sound signal indicating "set the rice cooker to the rice-cooking timer ON state".

Notification controller 16 may output the notification signal for notifying user U by all the speaker devices, i.e., speaker S1 and S2, and may output the notification signal for the notification by the speaker device in a specified room. For example, appliance determiner 15 may determine the room where user U is present based on the state information obtained by manager 12, and notification controller 16 may output the notification signal for notifying user U by the speaker device provided in the room that is determined by appliance determiner 15 as the room where user U is present.

Notification controller 16 can prohibit outputting the notification signal, when it is determined that the room where user U is present is a bedroom. In the case where user U sleeps in the bedroom, user U may have a reason for prioritizing the sleep. It may be improper to awake user U even in such a situation.

Appliance controller 17 is a functional unit that controls appliance D11 and so on. If sleep determiner 14 may determine that user U is sleeping, and appliance determiner 15 determines that the state information obtained by manager 12 matches normal information 20, appliance controller 17 performs control on appliance D11 and so on in the room where user U is present to cause the room to be appropriate for the sleep of user U.

A timing at which the notification based on the notification signal is performed is described.

Figure 3:
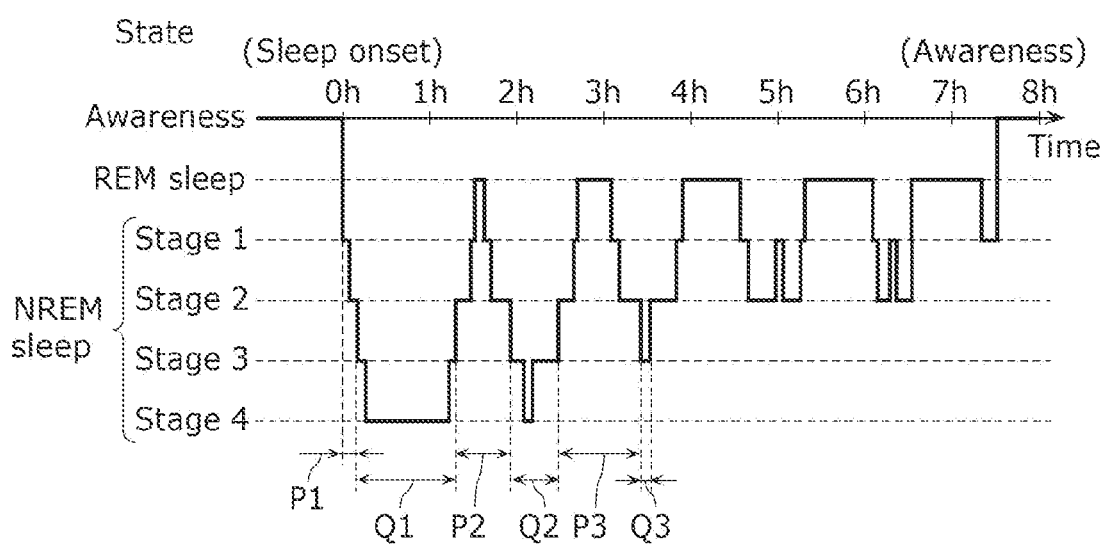
FIG. 3 is an explanatory view showing a sleeping curve of human beings.

FIG. 3 is an explanatory view showing a sleep curve of human beings. In FIG. 3, the vertical axis indicates a sleep state and the horizontal axis indicates time in which the sleep onset time is set zero (0 h). The sleep state indicated in the vertical axis is specified according to a brain wave, for example.

In general, the sleep states of human beings include rapid eye REM sleep and NREM sleep. In the NREM sleep, there are a plurality of stages from 1 to 4 according to depth of the sleep. Among stages 1 to 4, stage 1 indicates the lightest sleep and stage 4 indicates the deepest sleep.

When a person who awakes starts sleep, the sleep state changes from an awareness state to the NREM sleep at stage 1, followed by changing to stages 2, 3, and 4, in this order in the NREM sleep. In other words, when a person falls asleep, his/her sleep state may transition from the awareness state through the first sleep state to the second sleep state.

Here, regarding the sleep states of human beings, the first sleep state and the second sleep state are defined as follows. The first sleep state includes the NREM sleep state at stage 1 and stage 2. The second sleep state includes the NREM sleep state at stage 3 and stage 4. In other words, the second sleep state can be a deeper sleep state than the first sleep state. Accordingly, when user U falls asleep, the sleep state of user U transitions from the awareness state to the first sleep state, and then to the second sleep state. FIG. 3 shows terms P1, P2, and P3 that correspond to the first sleep state and periods Q1, Q2, and Q3 that correspond to the second sleep state.

FIG. 3 shows period Q1 at the initial stage of sleep from the sleep onset. In period Q1, growth hormone that may exercise an effect on human health matters, such as obesity, is actively secreted. The secretion of the growth hormone has an effect of improving the quality of sleep of user U. Accordingly, if user U takes period Q1 as long as possible, the growth hormone is actively secreted. On the other hand, if user U is forcibly awoken by the notification or the like during period Q1, period Q1 is shortened in the second sleep onset, causing the quality of sleep of user U to deteriorate.

Taking such transition in sleep states of human beings into account, sleep determiner 14 may determine whether the sleep state of user U is in the first sleep state based on the detected information obtained by obtainer 11. When sleep determiner 14 determines that the sleep state of user U is in the first sleep state, notification controller 16 may output the notification signal. More specifically, in the transition from the awareness state of user U through the first sleep state to the second sleep state, notification controller 16 may output the notification signal when determiner 13 determines that the sleep state of user U is in the first sleep state. This is for user U to be awoken for operating appliance D11 during a relatively light sleep state, i.e., before achieving a relatively deep sleep state, so that user U can have a continuing sleep for an appropriate length of time, thereafter. In addition, this may prevent a mistake in operations from occurring, which is caused by a low level of the awareness (or consciousness level) of user U when user U in a relatively deep sleep state is awoken by the notification.

FIG. 4 is an explanatory view showing an example of state information according to the present embodiment. The state information shown in FIG. 4 is obtained by manager 12 from appliance D11 and so on, and indicates the operation states of appliance D11 and so on.

As shown in FIG. 4, the state information includes information indicating the operation state of each of the one or more appliance D11 and so on. It is assumed that the information indicating the operation state is set to any one of the plurality of predetermined states for the respective appliance 11 and so on. For a rice cooker, for example, states of "timer ON", "rice cooking", "high-speed rice cooking", "keep warm", and so on may be predetermined as the plurality of states. For a dishwashing machine, for example, states of "washing", "drying", and so on may be predetermined as the plurality of the states. For a washing machine, for example, states of "timer ON", "washing", "stop", "stop (with laundry)" and so on may be predetermined as the plurality of the states.

FIG. 4 shows an example in which the rice cooker is in the keep warm state, the dishwashing machine is in the stop state, and the washing machine is in the stop state (here, laundry stays in a washing machine tub).

FIG. 5 is an explanatory view showing an example of the normal information according to the present embodiment. The normal information shown in FIG. 5 is predetermined information that indicates the normal operation state of appliance D11 and so on at the time when user U goes to bed.

Entries of the normal information shown in FIG. 5 include appliance names (illustrated as "Appliance" in FIG. 5) and the operation states.

The appliance names are respectively allocated to appliance D11 and so on. If there are a plurality of appliances of the same type in a residence of user U, identifiers that can respectively identify the plurality of appliances may be provided.

The operation state indicates a normal operation state of each of the appliances indicated by an appliance name in the entry.

The normal information may be previously set by user U in a manner that it is convenient for user U, or may be generated through learning processing or the like, based on user U's normal way to use appliance D11 and so on. If a use history of the appliance by user U proves that the state of the appliance at the time when user U goes to bed is a certain single state with a relatively high rate of days (for example, eight days per ten days, etc.), such a certain single state can be generated as the normal information.

FIG. 5 shows an example in which the rice cooker is in the rice cooking timer ON state, the dishwashing machine is in the washing state, and the washing machine is in the stop state.

When appliance determiner 15 performs determination as to the state information shown in FIG. 4 and the normal information shown in FIG. 5 and determines that the state information is different from the normal information in terms of at least one of the three appliances (i.e., rice cooker, dishwashing machine, and washing machine), notification controller 16 outputs the notification signal.

Processing performed by management apparatus 10 configured as above is described.

Figure 6:
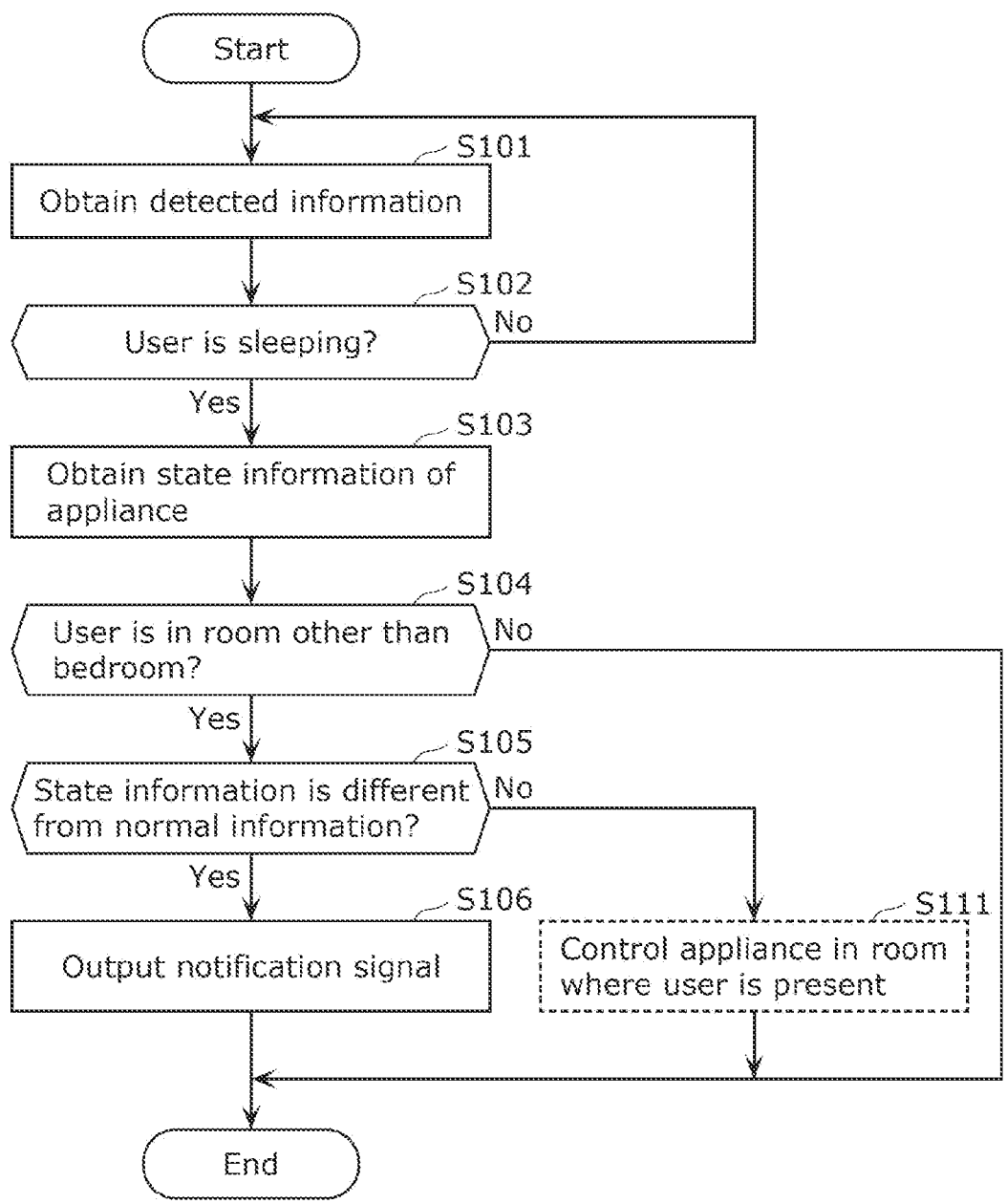
FIG. 6 is a flowchart showing processing performed by the management apparatus according to Embodiment 1.

FIG. 6 is a flowchart showing processing performed by management apparatus 10 according to the present embodiment.

In Step S101, obtainer 11 obtains the detected information from sensor SE.

In Step S102, sleep determiner 14 determines whether user U is sleeping based on the detected information that obtainer 11 has obtained in Step S101. If sleep determiner 14 determines that the user is sleeping (Yes in Step S102), the processing moves to Step S103. If not (No in Step S102), the processing in Step S101 is performed again.

In Step S103, manager 12 obtains the state information indicating the operation state of appliance D11 that user U uses.

In Step S104, appliance determiner 15 performs determination as to whether user U is present in a bedroom based on the detected information obtained by manager 12 in Step S103. If appliance determiner 15 determines that user U is in the bedroom (Yes in Step S104), the processing moves to Step S105. If not (No in Step S104), a series of the processing shown in FIG. 6 is terminated. In other words, notification controller 16 does not output the notification signal, i.e., notification controller 16 prohibits outputting the notification signal, when it is determined that user U is present is the bedroom.

In Step S105, appliance determiner 15 performs determination as to whether the state information obtained by manager 12 in Step S103 is different from the normal information. If appliance determiner 15 determines that the state information is different from the normal information (Yes in Step S105), the processing moves to Step S106. If not (No in Step S105), the processing moves to Step S111.

In Step S106, notification controller 16 outputs the notification signal. When the processing in Step S106 is terminated, a series of the processing shown in FIG. 6 is terminated.

In Step S111, appliance controller 17 controls appliance D11 and so on in a room where user U is present so that the room is appropriate for the sleep of user U. It should be noted that Step S111 may not be performed. When Step S106 is terminated, a series of the processing shown in FIG. 6 is terminated.

With the series of the processing shown in FIG. 6, management apparatus 10 appropriately awakes user U for the operation of appliance D11 and so on.

As mentioned above, in the management apparatus according to the present embodiment, the information processing apparatus detects that a user is sleeping and controls the outputting of the notification signal when the state of the appliance is different from the normal state. A situation in which a user is sleeping and the appliance state is different from the normal state occurs when the user falls asleep without performing setting of an appliance. In this case, if the user leaves the appliance as it is and continues sleeping, the appliance may not operate in accordance with the intension of the user. In such a case, the information processing apparatus causes the notification to be performed to the user, thereby awaking the user and encouraging the user to operate the appliance. Accordingly, information processing apparatus can appropriately awake user U for the operation of an appliance.

Furthermore, information processing apparatus stimulates the awareness of a user by the notification, when the sleep level of the user is the first sleep state in which the sleep depth is relatively light during the sleep of the user. In general, when a user is awoken from a sleep state in which the sleep depth is deep, it is difficult for the user to be awoken. If the user is awoken in such a situation, a level of the awareness (or consciousness level) is low. This may often cause a mistake in operations performed after the user awakes. In view of the above, a user is stimulated to awake during the first sleep state in which the sleep depth is relatively light, thereby appropriately encouraging the user to operate appliances after the user awakes.

Accordingly, the information processing apparatus can more appropriately awake a user for the operation of an appliance.

Furthermore, information processing apparatus stimulates the awareness of a user by the notification, when the user is in the first sleep state. Accordingly, a user can be stimulated to awake and to operate appliances as early a time as possible. Thus, a user can have, after the operation, a sleep for a continuing period of time in the second sleep onset. As mentioned above, the information processing apparatus can more appropriately awake a user for the operation of an appliance.

The information processing apparatus can appropriately awake a user for the operation of an appliance, in accordance with a sleep state of the user among the respective stages in the REM sleep and the NREM sleep.

The information processing apparatus performs the notification to a user using a speaker device in a room where the user is present. Accordingly, the user can be more appropriately awoken. In addition, the notification is not performed using a speaker device in a room different from the room where the user is present, thereby contributing to the reduction in throughput and power consumption. Accordingly, the information processing apparatus can more appropriately awake a user for the operation of an appliance.

Furthermore, the information processing apparatus refrains from performing the notification when a user is sleeping in a bedroom. In the case where a user is sleeping in a bedroom, the user may have a reason for prioritizing the sleep. It may be improper to awake the user even in such a situation. Accordingly, the information processing apparatus can awake a user for the operation of an appliance depending on a condition of the user.

Furthermore, when the state of an appliance matches the normal state, the information processing apparatus leaves the user to continuously sleep, and sets up an environment in which the user comfortably sleeps by controlling the appliances. Accordingly, the information processing apparatus can appropriately awake a user for the operation of an appliance, whereas it can appropriately leave the user to sleep when there is no need to operate appliances.

The information processing apparatus can appropriately awake a user for the operation of an appliance, in an easier manner using the heartbeat sensor, the acceleration sensor, the thermal image sensor, or the radio wave sensor.

Embodiment 2

In the present embodiment, an information processing apparatus that appropriately awakes user U for the operation of an appliance, and so on, is described using examples different from those of Embodiment 1. Specifically, if user U falls asleep in a state where the operation state of an appliance is different from the normal state, the information processing apparatus according to the present embodiment essentially awakes user U. Here, no problem may occur if user U operates an appliance after user U is awoken. In such a case, the information processing apparatus exceptionally performs control of refraining from awaking user U.

In the present embodiment, although the entire configuration of system 1 is the same as that in Embodiment 1, information contained in the normal information and determination processing by appliance determiner 15 using the normal information are different from those in Embodiment 1. Points different from those in Embodiment 1 are selectively described.

FIG. 7 is an explanatory view showing an example of the normal information according to the present embodiment. The normal information shown in FIG. 7 is predetermined for indicating a normal operation state of appliance D11 and so on, and includes a period of time (i.e., a normal period) in which appliance D11 and so on should be in such a normal operation state.

Entries of the normal information shown in FIG. 7 include appliance names (shown as "Appliance" in FIG. 7), the operation state, a normal start-time, and a normal end-time.

The appliance names and the operation states are the same as the information shown in FIG. 5.

The normal start-time is a time point indicating the start of the normal period in which appliances indicated by the appliance names in the entries should be in the normal state.

The normal end-time is a time point indicating the end of the normal period in which appliances indicated by the appliance names in the entries should be in the normal state.

It should be noted that the normal end-time is optional. If the normal end-time is not set, the moment of the normal start-time or a relatively short period (i.e., several seconds or several minutes) including the normal start-time is set as the normal period.

For example, FIG. 7 shows that: the rice cooking timer of a rice cooker is ON in the normal period from 23:00 to 6:00 the next day; the dishwashing machine is in an operation state in the normal period from 22:00 to 3:00 the next day; and the washing machine is in the stop state in the normal period at 18:00.

In this case, sleep determiner 14 obtains a sleep start time that is the time point at which the sleep state of user U transitions from an awareness state to a first sleep state (i.e., the time point at which user U starts sleeping) based on the detected information obtained by obtainer 11. Sleep determiner 14 determines (a) whether the state information at the obtained sleep start time is different from the normal information and (b) whether a sleep end presumption time at which a normal sleep period has been elapsed from the obtained sleep start time is later than the normal period. Here, the sleep end presumption time is an estimated value in terms of the time point at which user U terminates sleeping and awakes. The normal sleep time is a duration in which user U sleeps in a normal time. The normal sleep time may be individually set for each user U, or may be a typical sleeping time (e.g., seven hours).

When sleep determiner 14 determines that the state information is different from the normal information for the above (a), and the sleep end presumption time is later than the normal period for the above (b), notification controller 16 outputs a notification signal.

Then, processing performed by management apparatus 10 is described.

Figure 8:
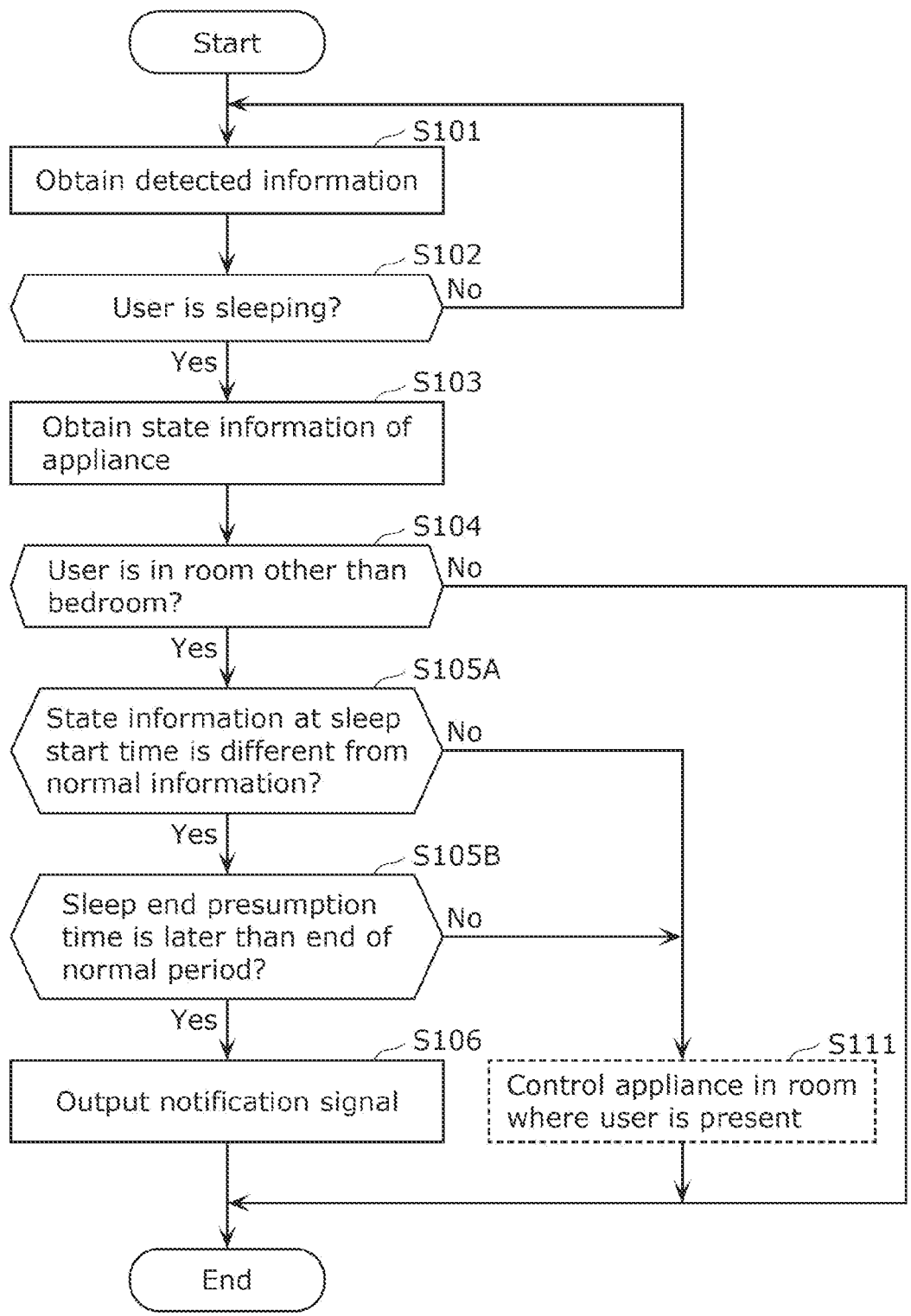
FIG. 8 is a flowchart showing processing performed by a management apparatus according to Embodiment 2.

FIG. 8 is a flowchart showing processing performed by management apparatus 10 according to the present embodiment. In the flowchart shown in FIG. 8, the processing in Steps S101 to S104, S106, and S111 are the same as the processing in Embodiment 1 (see FIG. 6), and thus detailed description is omitted.

Through Steps S101 to S104, as in Embodiment 1, when sleep determiner 14 determines that user U sleeps based on the detected information, and appliance determiner 15 determines that user U is present in a room other than a bedroom, processing in Step S105A is performed.

In Step S105A, appliance determiner 15 performs determination as to whether the state information at the sleep start time is different from the normal information. If appliance determiner 15 determines that the state information is different from the normal information (Yes in Step S105A), the processing moves to Step S105B. If not (No in Step S105A), the processing moves to Step S111.

In Step S105B, appliance determiner 15 performs determination as to whether the sleep end presumption time is later than the end of the normal period. If appliance determiner 15 determines that the sleep end presumption time is later than the end of the normal period (Yes in Step S105B), the processing moves to Step S106. If not (No in Step S105B), the processing moves to Step S111.

In Step S106, notification controller 16 outputs the notification signal, in the same manner as in Embodiment 1. When Step S106 is terminated, a series of the processing shown in FIG. 6 is terminated.

In Step S111, appliance controller 17 controls appliances in a room where user U is present so that the room is suitable for the sleep of user U, similarly to the case in Embodiment 1. It should be noted that Step S111 may not be performed. When Step S111 is terminated, a series of the processing shown in FIG. 6 is terminated.

Subsequently, two cases regarding the determination processing that appliance determiner 15 performs using the normal information are described. Specifically, results of the determination performed by appliance determiner 15 are described in terms of two patterns that are different from each other in relation between the sleep end presumption time and the normal period are described. Here, a normal sleep time is set to seven hours.

(1) Case in which Sleep End Presumption Time is Later than Normal Period

Figure 9:
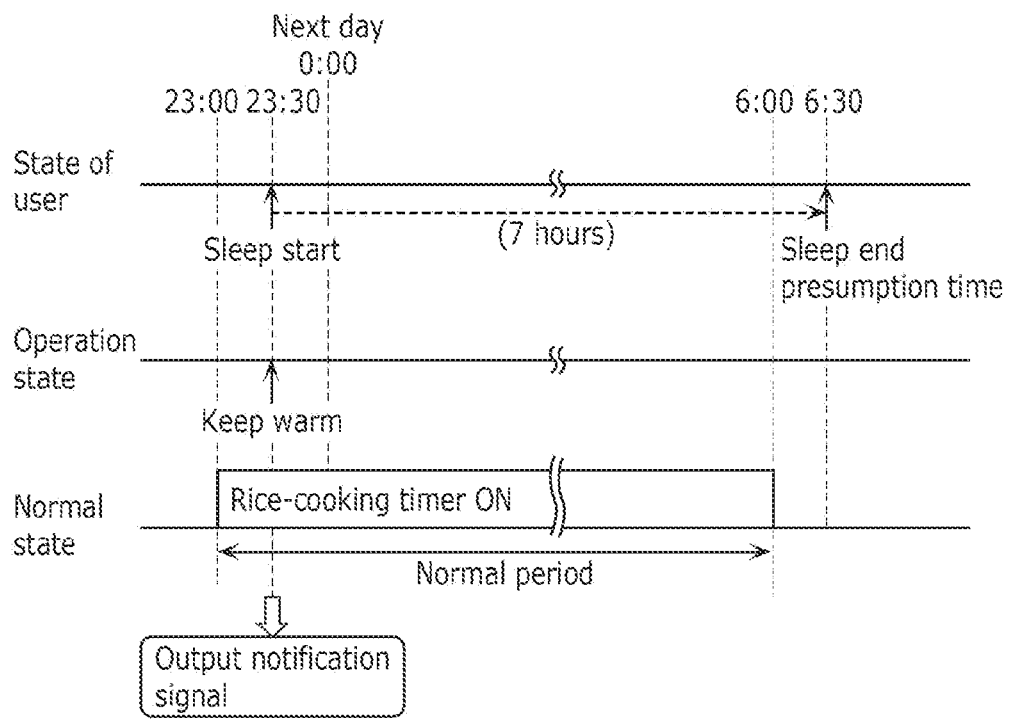
FIG. 9 is an explanatory view showing a first example of determination by an appliance determiner according to Embodiment 2.

FIG. 9 is an explanatory view showing a first example of the determination performed by appliance determiner 15 according to the present embodiment. The sleep end presumption time of user U, which is shown in FIG. 9, is after the normal period. In addition, the operation state of a rice cooker at the time when user U starts sleeping is a keep-warm state, which is different from a rice-cooking timer ON state indicated in the normal information.

In this case, appliance determiner 15 determines that the state information at the sleep start time is different from the normal information (Yes in Step S105A), and determines that the sleep end presumption time is after the normal period (Yes in Step S105B). As a result, notification controller 16 determines outputting the notification signal.

This is for preventing such a situation by awaking user U, since if user U awakes at the sleep end presumption time, the period in which the rice cooking timer of the rice cooker should be ON already elapses.

(2) Case in which Sleep End Presumption Time is within Normal Period

Figure 10:
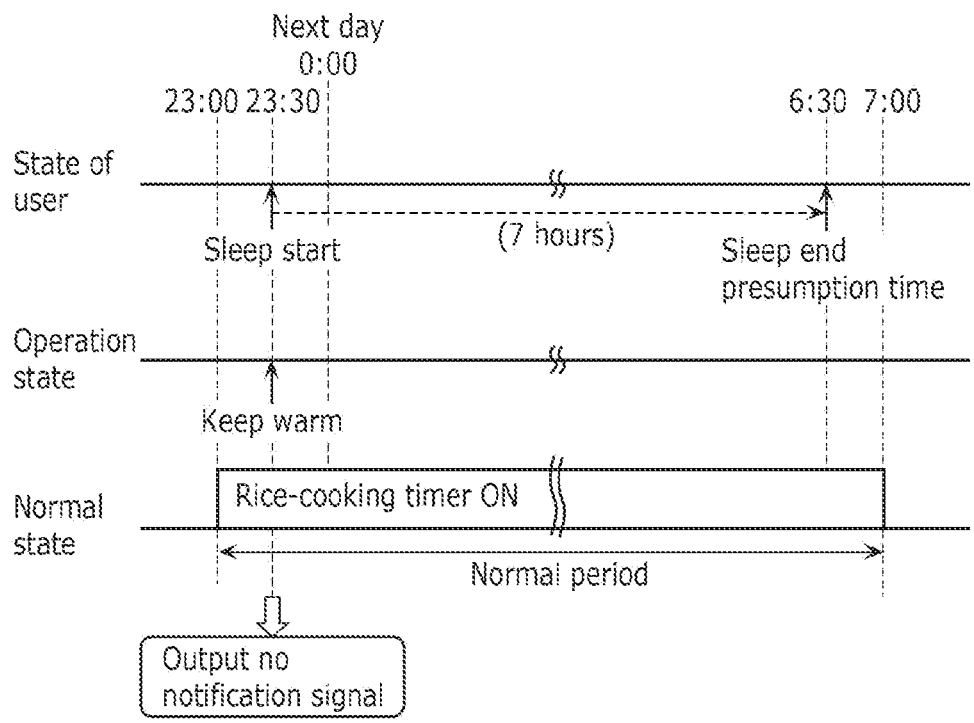
FIG. 10 is an explanatory view showing a second example of the determination by the appliance determiner according to Embodiment 2.

FIG. 10 is an explanatory view showing a second example of the determination performed by appliance determiner 15 according to the present embodiment. The sleep end presumption time of user U, which is shown in FIG. 10, is within the normal period. In addition, the operation state of the rice cooker at the time when user U starts sleeping is the keep-warm state, which is different from the rice-cooking timer ON state indicated in the normal information.

In this case, appliance determiner 15 determines that the state information at the sleep start time is different from the normal information (Yes in Step S105A), and determines that the sleep end presumption time is not later than the end of the normal period (No in Step S105B). As a result, notification controller 16 determines not to output the notification signal.

This is for allowing user U to merely operate the rice cooker to turn ON after awaking, since if user U starts sleeping at the sleep start time and awakes at the sleep end presumption time, the period in which the rice cooking timer of the rice cooker should be ON does not elapse.

Although the relation of management apparatus 10 with a single user U and a residence of user U is described in the present embodiment, management apparatus 10 can be connected to appliances in residences of a plurality of users U via network N, and can perform processing of awaking the plurality of users U. In this case, the number of management apparatus 10 can be reduced than the number of user U or the number of the residence. Accordingly, the processing load of management apparatus 10 can be reduced and the power consumption can be reduced. Furthermore, resources and cost for producing, operating, and maintaining management apparatus 10 can also be reduced.

As mentioned above, in the information processing apparatus according to the present embodiment, if user U falls asleep when the operation state of the appliance is different from the normal state, the information processing apparatus essentially awakes user U. However, if no problem occurs with user U operating appliances after he/she awakes, the information processing apparatus performs control so as not to awake user U exceptionally. This is because, if no problem occurs with user U operating appliances after he/she awakes, there is no need to awake the user at the time when the user starts sleeping for the operation of an appliance. Accordingly, the information processing apparatus can more appropriately awake a user for the operation of an appliance.

Modification 1 of Each Embodiment

In the modification, configurations different from those in system 1 in the respective embodiments are described.

Figure 11:
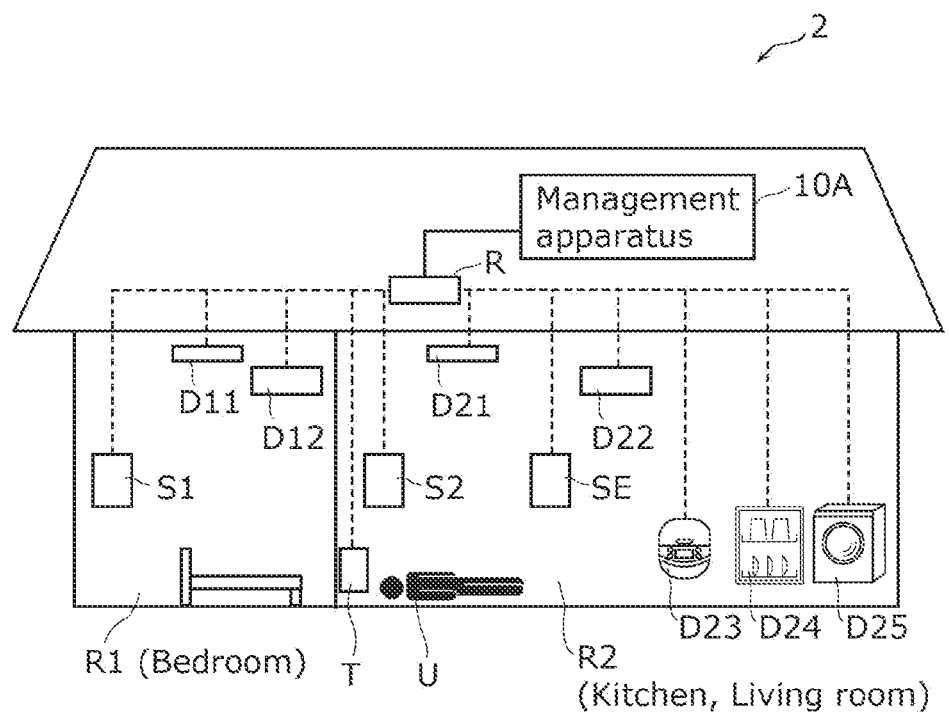
FIG. 11 is an explanatory view schematically showing a configuration of a system according to Variation 1 of each of the embodiments.

FIG. 11 is an explanatory view schematically showing a configuration of system 2 according to the present modification.

In system 2 shown in FIG. 11, management apparatus 10 in the respective embodiments above is provided as management apparatus 10A, in a residence of user U. It is intended that management apparatus 10A is to be used by user U. In other words, it is not intended that management apparatus 10A is used by other users. Accordingly, it is assumed that a single management apparatus 10A is provided in a single residence.

The configurations of an appliance and a device, which constitute system 2, are the same as those described in the respective embodiments.

In the configuration according to the present modification, management apparatus 10A can awake user U without using network N. Accordingly, even if failures occur in network N, management apparatus 10A can operate with no problem. In addition, management apparatus 10A is merely required to have functions for a single user U and his/her residence. Accordingly, the processing load of the information processing and the power consumption of management apparatus 10A can be reduced. Furthermore, management apparatus 10A can be mounted to appliance D11 and so on as one of functions.

Modification 2 of Each Embodiment

In the present modification, configurations different from those in system 1 in the respective embodiments above are described.

Figure 12:
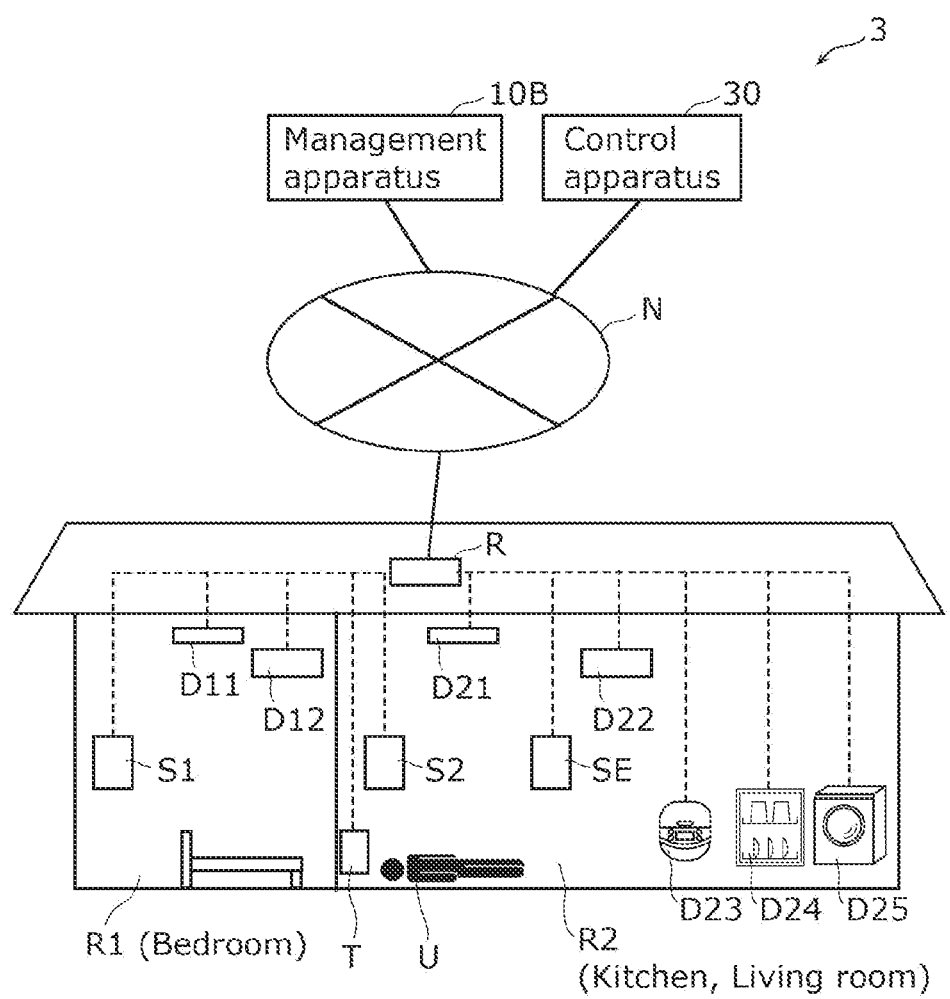
FIG. 12 is an explanatory view schematically showing a configuration of a system according to Variation 2 of each of the embodiments.
Figure 13:
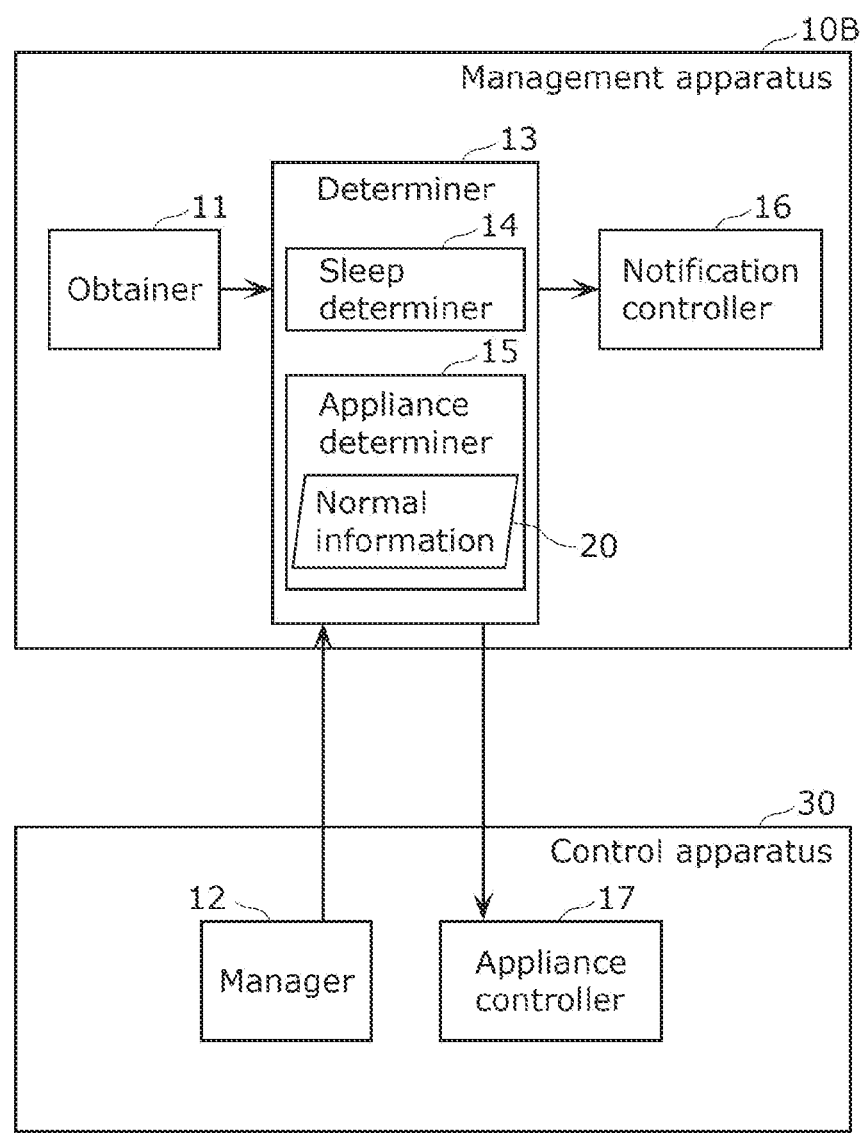
FIG. 13 is an explanatory view schematically showing configurations of a management apparatus and a control apparatus according to Variation 2 of each of the embodiments.

FIG. 12 is an explanatory view schematically showing a configuration of system 3 according to the present modification. FIG. 13 is an explanatory diagram schematically showing configurations of management apparatus 10B and control apparatus 30, according to the present modification.

As shown in FIG. 12, system 3 includes: management apparatus 10B; control apparatus 30, appliance D11 and so on; speaker S1 and so on; and sensor SE.

Appliance D11 and so on, speaker S1 and so on, and sensor SE are the same as those in each embodiment above.

Management apparatus 10B and control apparatus 30 are connected to each other via network N in a communicable manner.

As shown in FIG. 13, management apparatus 10B includes obtainer 11, determiner 13, and notification controller 16. Management apparatus 10B corresponds to management apparatus 10, according to each embodiment above, without including manager 12 and appliance controller 17.

Control apparatus 30 includes manager 12 and appliance controller 17. Manager 12 and appliance controller 17 are functional units respectively the same as manager 12 and appliance controller 17 of management apparatus 10 according to each embodiment above.

In other words, management apparatus 10B and control apparatus 30 share the functions of management apparatus 10 according to each embodiment above.

In the configuration according to the present modification, management apparatus 10B can awake user U, using control apparatus 30, for the operation of appliance D11 and so on.

In particular, it is advantageous for system 3 that management apparatus 10B can be additionally provided to a system in which control apparatus 30 dedicated to manage or control appliance D11 and so on is already provided.

As mentioned above, embodiments are described as examples of technique of the present disclosure. For the description, the accompanied drawings and detailed description are provided.

In view of the above, structural components described in the accompanied drawings and the detailed description may include structural components that are not necessary for achieving the object but are for exemplifying the embodiments, in addition to structural components that are necessary for achieving the object. Accordingly, it should not be recognized immediately that these unnecessary structural components are necessary, by the accompanied drawings and the detailed description in which these unnecessary structural components are shown and described.

In addition, the embodiments are for exemplifying technique of the present disclosure, and thus various change, replacement, addition, omission, and so on can be conducted in scope of claims and a range equivalent thereto.

INDUSTRIAL APPLICABILITY

The present disclosure is applicable to a control apparatus that controls appliances.

REFERENCE SIGNS LIST 1, 2, 3 System
10, 10A, 10B Management apparatus
11 Obtainer
12 Manager
13 Determiner
14 Sleep determiner
15 Appliance determiner
16 Notification controller
17 Appliance controller
20 Normal information
30 Control apparatus
D11, D12, D21, D22, D23, D24, D25 Appliance
N Network
P1, P2, P3, Q1, Q2, Q3 Period
R Router
R1, R2 Room
S1, S2 Speaker
SE Sensor
T Terminal
U User

The invention claimed is:

1. An information processing apparatus comprising:
an obtainer that obtains detected information from a sensor that detects sleep of a user;
a first determiner that determines whether the user is currently in a sleep state, based on the detected information;
a manager that is connected to an appliance via a network, and obtains state information indicating current operation information of the appliance;

a second determiner that determines whether the state information indicating the current operation information of the appliance obtained by the manager is different from predetermined normal information indicating a normal operation state of the appliance that is a state of the appliance when the user goes to bed based on a history of normal use of the appliance by the user; and a notification controller that outputs a notification signal to a speaker that outputs sound to the user who is in the sleep state, when the second determiner determines that the state information indicating the current operation information of the appliance is different from the normal information of the appliance when the user is in a normal sleep state, wherein the notification signal is a signal that stimulates the user to awaken.

2. The information processing apparatus according to claim 1, wherein the first determiner further determines whether the sleep state of the user is a first sleep state, based on the detected information obtained by the obtainer, and the notification controller outputs the notification signal, when the first determiner determines that the sleep state of the user is the first sleep state.

3. The information processing apparatus according to claim 2, wherein the notification controller outputs the notification signal, when the first determiner determines that the sleep state of the user is the first sleep state, in a transition of a sleep state of the user from an awareness state, through the first sleep state, to a second sleep state, the second sleep state being a state of deeper sleep than the first sleep state.

4. The information processing apparatus according to claim 3, wherein the first sleep state includes a non-rapid eye movement (NREM) sleep state at stage 1 and stage 2, and the second sleep state includes a NREM sleep state at stage 3 and stage 4.

5. The information processing apparatus according to claim 2, wherein the normal information includes a normal period in which the appliance should be operating in the normal operation state, the first determiner further:
obtains a sleep start time at which a state of the user transitions from an awareness state to the first sleep state, based on the detected information obtained by the obtainer; and makes a first determination as to whether the state information at the sleep start time obtained is different from the normal information, and a second determination as to whether a sleep end presumption time at which a normal sleep period has elapsed from the sleep start time obtained is later than the normal period, and the notification controller outputs the notification signal, when the first determiner determines, regarding the first determination, that the state information is different from the normal information, and determines, regarding the second determination, that the sleep end presumption time is later than the normal period.

6. The information processing apparatus according to claim 1, wherein the second determiner further determines a room where the user is present, based on the state information obtained by the manager, and the notification controller outputs the notification signal for notifying the user, via a speaker provided in the room where the user is present.

7. The information processing apparatus according to claim 6, wherein the notification controller prohibits outputting the notification signal when the user is determined to be present in a bedroom.

8. The information processing apparatus according to claim 1, further comprising:

an appliance controller that causes the appliance in a room where the user is present to set an environment in the room to be suitable for the sleep of the user, when the first determiner determines that the user is in the sleep state and the second determiner determines that the state information obtained by the manager matches the normal information.

9. The information processing apparatus according to claim 1, wherein the sensor includes at least a heartbeat sensor, an acceleration sensor, a thermal image sensor, or a radio wave sensor.

10. An information processing method comprising:

obtaining detected information from a sensor that detects sleep of a user;

first determining whether the user is currently in a sleep state, based on the detected information;

obtaining state information indicating current operation information of an appliance connected to a network;

second determining whether the state information indicating the current operation information of the appliance obtained by the manager is different from predetermined normal information indicating a normal operation state of the appliance that is a state of the appliance when the user goes to bed based on a history of normal use of the appliance by the user; and outputting a notification signal to a speaker that outputs sound to the user who is in the sleep state, when it is determined that the state information indicating the current operation information of the appliance is different from the normal information of the appliance when the user is in a normal sleep state in the second determining, wherein the notification signal is a signal that stimulates the user to awaken.

11. The information processing apparatus according to claim 1, wherein the state information indicating the current operation information of the appliance obtained by the manager is reservation information of operation of the appliance.

12. The information processing method according to claim 10, wherein the state information indicating the current operation information of the appliance is reservation information of operation of the appliance.

* * * * *